(12) United States Patent
Hipps et al.

(10) Patent No.: US 6,228,025 B1
(45) Date of Patent: *May 8, 2001

(54) ILLUMINATED SAPHENOUS VEIN RETRACTOR

(75) Inventors: W. Michael Hipps, Augusta; Robert F. Campbell, Atlanta, both of GA (US)

(73) Assignee: Genzyme Corporation, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/071,786

(22) Filed: May 1, 1998

(51) Int. Cl.$^7$ .................................................. A61B 17/00
(52) U.S. Cl. ........................ 600/213; 600/210; 600/226; 600/235; 600/245; 600/246
(58) Field of Search .................................. 600/201, 210, 600/212, 213, 214, 226, 235, 245, 246

(56) References Cited

U.S. PATENT DOCUMENTS

| | | |
|---|---|---|
| 4,052,980 | 10/1977 | Grams et al. . |
| 4,597,030 | 6/1986 | Brody et al. . |
| 4,765,701 | 8/1988 | Cheslak . |
| 4,836,190 * | 6/1989 | Zwick ................................... 600/226 |
| 4,996,976 | 3/1991 | Nakagawa . |
| 5,005,108 | 4/1991 | Pristash et al. . |
| 5,035,232 | 7/1991 | Lutze et al. . |
| 5,514,076 | 5/1996 | Ley . |
| 5,514,077 | 5/1996 | Rabban . |
| 5,667,480 | 9/1997 | Knight et al. . |
| 5,722,934 | 3/1998 | Knight et al. . |
| 5,725,479 | 3/1998 | Knight et al. . |
| 5,730,748 | 3/1998 | Fogarty et al. . |
| 5,776,159 | 7/1998 | Young . |
| 5,797,947 | 8/1998 | Mollenauer . |
| 5,853,417 | 12/1998 | Fogarty et al. . |
| 5,904,650 | 5/1999 | Wells . |
| 5,913,818 | 6/1999 | Co et al. . |
| 5,921,919 | 7/1999 | Chin et al. . |
| 5,967,971 | 10/1999 | Bolser . |
| 6,007,487 * | 12/1999 | Foley et al. ....................... 600/210 X |
| 6,033,361 * | 3/2000 | Co et al. ............................ 600/210 |

FOREIGN PATENT DOCUMENTS

2133694 * 8/1984 (GB) .................................... 600/245
WO 99/01696 1/1999 (WO) .

OTHER PUBLICATIONS

Snowden Pencer DSP, The Diamond–Line of Surgical Instruments Brochure, Tebbetts EndoPlastic Instrument System, 1995.

(List continued on next page.)

Primary Examiner—Jeffrey A. Smith
(74) Attorney, Agent, or Firm—Richard D. Allison; Thomas J. DesRosier

(57) ABSTRACT

A illuminated surgical retractor for illuminating a subcutaneous surgical field in the space between a vessel, such as the saphenous vein, and the subcutaneous tissue when the illuminated retractor is used to retract the subcutaneous tissue away from the superior surface of the vessel, the illuminated surgical retractor having a handle connected at an acute angle to a distal end of a first blade section, a second blade section that is connected, and substantially co-planer, to the first blade section, a distal end of the second blade section defining an illumination input end, a connector coupled to the illumination input end so that a source of illumination can be optically coupled, via the connector, to the illumination input end so that the second blade section is substantially illuminated, and, alternatively, a bent tip extending from the proximal end of the first blade section to aid in the required dissection of the intervening tissue.

43 Claims, 5 Drawing Sheets

OTHER PUBLICATIONS

Snowden Pencer DSP, EndoCABG System, Innovative Instrumentation for Endoscopic Coronary Artery Bypass, Grafting, 1996.

Design News, Medical Plastics/Cover Story, Bypass Surgery Made Easier, Disposable Instruments Made From Standard Plastics, Key to Minimally Invasive Procedure for Extracting Veins, Gary Chamberlain, Senior Editor, pp. 57–58; 60, 62 (Jan. 6, 1997).

Lee, John, Surgical Physician Assistant, Minimally Invasive Vein Harvesting, Nov./Dec. 1996, pp. 26–32.

Auto Suture Company, The Mini–Harvest System for Minimally Invastive Saphenous Vein Harvesting, 1996.

Dregelid, E. et al., Endothelial Cell Injury in Human Saphenous Veins After Manipulating and Tweezer Grasping, J. Cardiovasc. Surg., vol. 29, pp. 464–469 (1988).

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

Gundry, Steven R., et al., Optimal Preparation Techniques for Human Saphenous Vein Grafts, Surgery, No. 6, pp. 785–794, (Dec. 1980).

Hauer, G. et al., Endoscopic Subfascial Discission of Perforating Veins, Surg. Endosc., vol. 2, pp. 5–12 (1988).

Meldrum–Hanna, W. et al., Long Saphenous Vein Harvesting, Aust. N.Z.J. Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 (Feb. 1984).

Wheatley, D.J., Autocoronary Bypass Grafting Techniques, Surgery of Coronary Artery Disease, pp. 348–349 (Date Unknown).

* cited by examiner

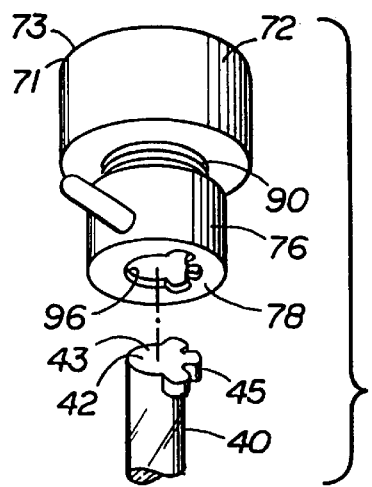 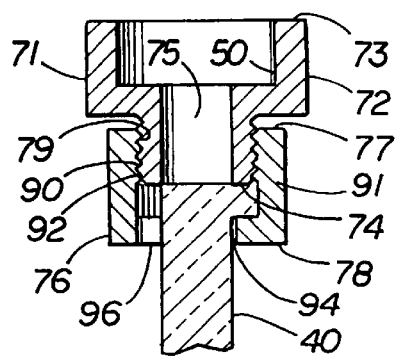
FIG. 5A FIG. 5B
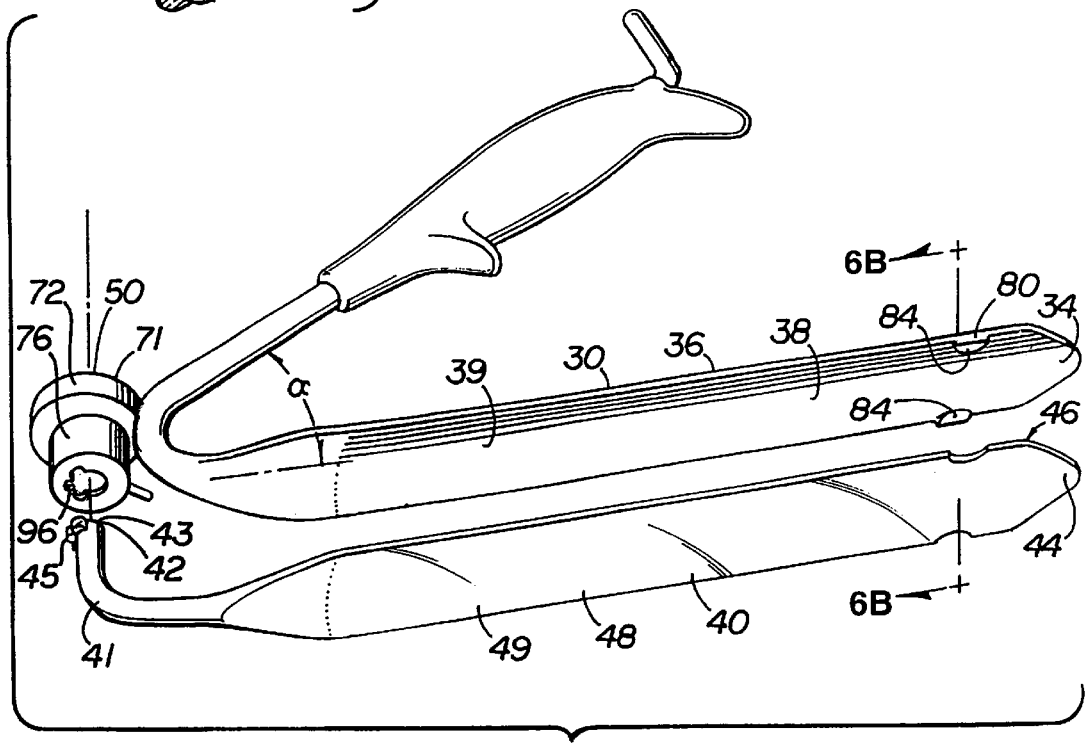
FIG. 6A
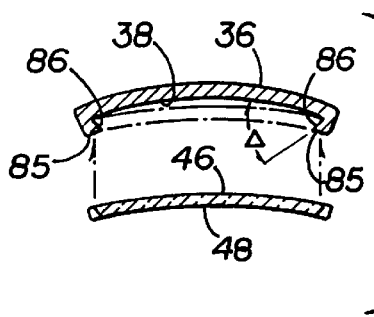
FIG. 6B

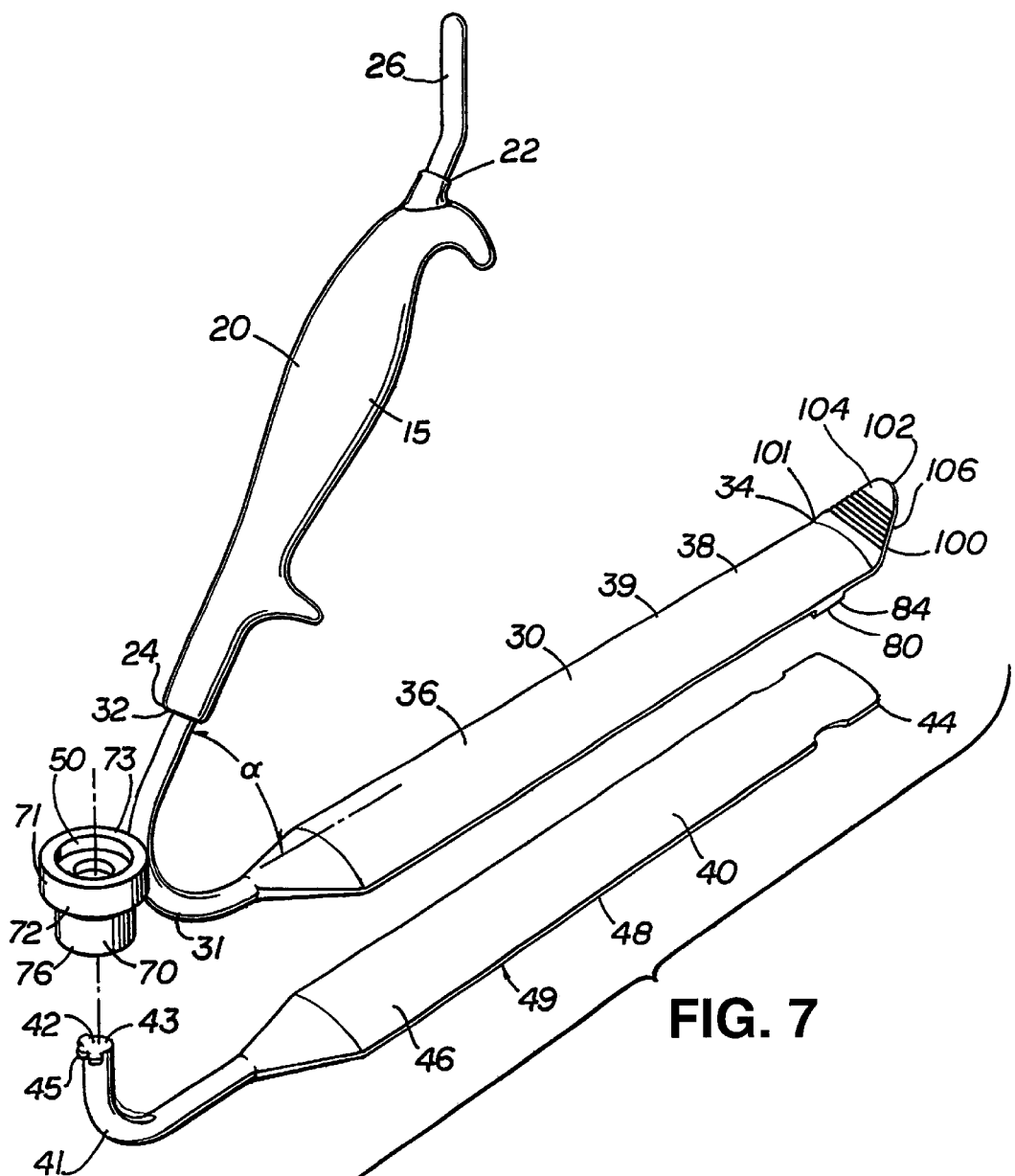
FIG. 7
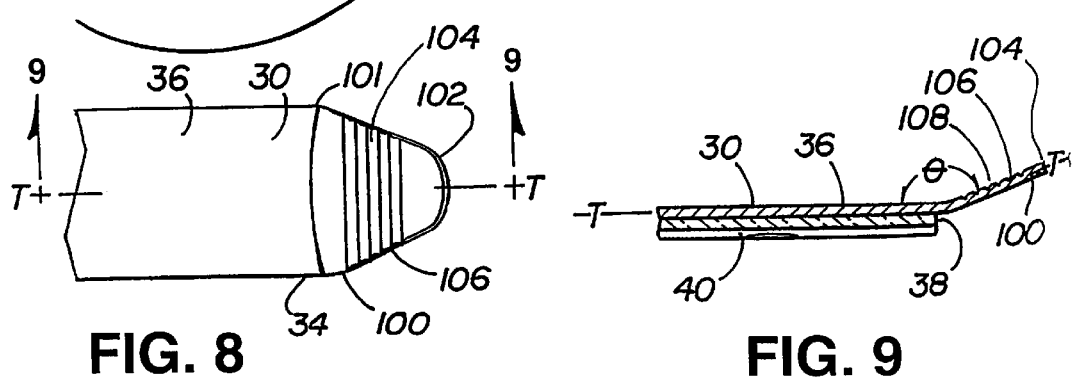
FIG. 8
FIG. 9

ILLUMINATED SAPHENOUS VEIN RETRACTOR

BACKGROUND OF THE INVENTION

1. Field of the Invention

The present invention relates, in general, to vessel harvesting and, in particular, to a new and useful illuminated retractor for creating a working space for dissecting instruments in support of a surgical procedure such as a coronary bypass procedure or other type of vessel harvest procedures.

2. Background Art

In certain surgical procedures, it is necessary to remove a section of a blood vessel from a patient for use in another part of the patient's body or for transplanting into a second patient's body. For example, a section of the saphenous vein may be removed for use in coronary bypass surgery to replace coronary arteries which supply blood to the heart. As a result of aging and disease, coronary arteries may become blocked by plaque deposits, stenosis, or cholesterol. In some instances, these blockages can be treated with angioplasty, atherectomy or stent placement, and coronary bypass surgery is not required. Coronary bypass surgery is required when these other methods of treatment cannot be used or have failed to clear the blocked artery.

In the coronary bypass surgery, a vein is harvested from elsewhere in the body and grafted into place between the aorta and the coronary artery beyond the point of blockage. It is preferred to use a vein taken from the patient undergoing the bypass surgery since the patient is a ready source of suitable veins that will not be rejected by the body after transplantation. The saphenous vein in the leg is typically the best substitute for small arteries such as the coronary arteries because the saphenous vein is typically 3 to 5 mm in diameter (about the same size as the coronary arteries) and it is thus the preferred vein for use in coronary bypass surgery. Also, the venous system of the legs is sufficiently redundant so that after removal of the saphenous vein, other veins that remain in the leg are adequate to provide adequate return blood flow. The cephalic vein in the arm is an alternative that is sometimes used.

The conventional, non-endoscopic, surgical procedure for the removal of the long saphenous vein as a graft in coronary and vascular surgery may require the surgeon to make one long incision from the groin to the knee or the ankle of the patient's leg to allow access to the saphenous vein. Alternatively, if the surgeon uses several long incisions, one or more small skin bridges are left along the line of the incisions. While handling of the vein should be kept to a minimum, the vein must be separated from the connective tissue, and that requires the application of some force. After exposing the vein, the surgeon grasps it with his fingers while stripping off the surrounding tissues with dissecting scissors or other scraping instruments. The surgeon uses his fingers and/or blunt dissection tools to separate the vein from the surrounding tissue. To reach under the small skin bridges, the surgeon lifts the skin with retractors and dissects the vein free. When the vein has been completely separated from the surrounding tissue and the tributary veins that feed into the saphenous vein, the surgeon cuts the proximal and distal ends of the vein and removes the vein from the leg. After removal, the vein is prepared for implantation into the graft site and the long incisions made in the leg are closed, for example by suturing or staples.

As can be seen from the description of the conventional, non-endoscopic, vessel harvesting operation, the vessel harvesting operation is very traumatic in its own right. In the case of coronary artery bypass, this operation is carried out immediately before the open chest operation required to graft the harvested vein into the coronary arteries. Unfortunately, the vein harvesting operation is often the most troublesome part of the operation for the patent. The long incision, or incisions, involves the risk of injury to the medial lymph bundle and the risk of infection of the extensive operation site itself. The leg may thus, in addition to being very painful, be slow to heal, or may not heal properly, especially with those patients who have poor circulation in their extremities, and can consequently hinder the patient's recover from the operation. It is therefore desirable to perform the vessel harvesting procedure in as minimally invasive a manner as feasible.

One alternative for minimally invasive vessel harvesting uses an endoscopically controlled vessel removal. In contrast to the open long incision method, the surgeon can limit himself to 2–3 small incisions on the proximal thigh, at the level of the knee joint and perhaps the inner malleolus. Such minimally invasive or endoscopic vessel harvesting is known in the surgical field. Viewing the tools through an endoscope or laparoscope, or a video display from the endoscope, the surgeon typically grasps and holds the saphenous vein with a grasper which is introduced through the lumen of an endoscope. After connective tissue is dissected from around the vein, the vein is ligated and transected and removed via the lumen of the endoscope. Alternatively, as the vein is withdrawn into the lumen of the endoscope, the endoscope may be maneuvered along the length of the vein while side branches of the vein are ligated and transected whenever encountered. The endoscopic removal methods leave tissues intact and the vein is prepared and removed under visual conditions. With the same operating time relative to the vein harvesting, postoperative complaints and the risk of wound infection are considerably less than with the conventional, non-endoscopic, procedure.

There are several drawbacks to the endoscopic vessel harvesting method described above. First, the endoscopic or laproscopic methods require the surgeon to view the tools and the operating field through the distorted visual perspective provided by the endoscope, laparoscope, or the video display from the endoscope, which is a poor substitute for the actually visualization of the surgical field by the surgeon's naked eye. Second, compounding the first drawback, in practicing this method there is limited visibility of the saphenous vein and its side branches because viewing is limited to the immediate area directly in front of the endoscope. Third, the illumination within the subcutaneous space created by this type of endoscope is also limited to the light emitted directly at the distal portion of the endoscope. Another drawback to this type of procedure is that the side branches of the saphenous vein limit the maneuverability of the endoscope since the outer edge of the endoscope body is prevented from advancing along the trunk of the saphenous vein until the encountered side branches are ligated and transected thereby. Once freed, the endoscope is then maneuvered until the next side branch is encountered. Moreover, it has been found that methods that utilize this type of endoscope, i.e. an endoscope having a lumen, provide a working space that is very restricted because the side walls of the scope body constrain the working instrumentation to a limited area. It would be desirable to use a procedure that overcomes the drawbacks inherent to the endoscopic vessel harvesting method.

In an alternative minimally invasive technique for harvesting a blood vessel that overcomes the drawbacks of the endoscopic method, the surgeon utilizes 2–3 small incisions on the proximal thigh, at the level of the knee joint and perhaps the inner malleolus, which results in several long skin bridges between the incisions. To reach under the skin bridges, the surgeon lifts the skin with retractors and exposes the vein. After exposing the vein, the surgeon uses his fingers and/or blunt dissection tools to separate the vein from the surrounding tissues. It is desirable for the retractor to have some means of aiding the dissection of the surrounding tissues so that the trauma and time required for the procedure is limited. When the vein has been completely separated from the surrounding tissue and the tributary veins that feed into the saphenous vein, the surgeon cuts the proximal and distal ends of the vein and removes the vein from the leg. After removal, the vein is prepared for implantation into the graft site, and the 2–3 small incisions made in the leg are sutured or stapled closed. Because the dissection of the vein is accomplished by the surgeon's fingers and/or by blunt dissection, this technique may be accomplished by the surgeon in a more timely manner than the endoscopic method. This alternative technique is a minimally invasive technique that, just like the endoscopic method described above, consequently minimizes the risks and complications of the surgery.

This technique overcomes the endoscopic method drawbacks of limited movement and limited workspace of the procedure enabling instrumentation and the limited and distorted visual perspective provided by the endoscope, laparoscope, or the video display from the endoscope. However, one drawback remains. Using prior art retractors, the illumination of the surgical field is poor. By necessity of the minimally invasive nature of the procedure, the vessel harvesting procedure is primarily conducted under the long skin bridges left between the small incisions. Because the skin bridges are so long, it is difficult to sufficiently illuminate the subcutaneous space between the vessel and the subcutaneous tissue when retractors known in the art are used to retract the tissue away from the superior surface of the vessel. With insufficient illumination of the surgical field, the advantages of the surgeon being able to maneuver freely and to optically visualize the surgical field using the benefit of his own binocular vision during the course of the minimally invasive procedure are eroded. It is therefore desirable to provide a means of providing illumination to the subcutaneous space formed by the retractor so that the surgeon can efficiently view and operate in the entire surgical field exposed by the retractor.

SUMMARY OF THE INVENTION

The present invention overcomes the disadvantages of the prior art. Specifically, as best shown in FIGS. 1 and 2A, the present invention provides for an illuminated retractor for illuminating the subcutaneous space between a vessel, such as the saphenous vein which is located in a patient's leg, and the subcutaneous tissue when the illuminated retractor is used to retract the tissue away from the superior surface of the vessel.

In the contemplated minimally invasive operation for harvesting a blood vessel, the surgeon utilizes 2–3 small incisions on the proximal thigh, at the level of the knee joint and perhaps the inner malleolus which results in several long skin bridges between the incisions. To expose the length of the vein remaining under the long skin bridges, the surgeon lifts the skin and the subcutaneous tissue with the illuminated retractor. The illuminated retractor provides a large, well illuminated surgical field, extending the substantial length of the retractor within the subcutaneous space created by the retractor. With the vein thus exposed, the surgeon uses his fingers and/or blunt dissection tools to separate the vein from the surrounding tissues. When the vein has been completely separated from the surrounding tissue and the tributary veins that feed into the saphenous vein, the surgeon cuts the proximal and distal ends of the vein and removes the vein from the leg. After removal the 2–3 small incisions made in the leg are sutured or stapled closed and the vein harvesting procedure is completed.

The illuminated surgical retractor has a handle, a first blade section, a second blade section, and a connector. The handle, which is preferably contoured to be gripped by the operating surgeon, is connected to the first blade section at the distal end of the first blade section, thus permitting one-handed use by the surgeon. The handle permits the retractor to be lifted at any angle with respect to the axis of the vein and, when a pulling force is applied to the handle, a corresponding pulling or retractive force is applied to the subcutaneous tissue via the first blade section, which creates the subcutaneous space beneath the subcutaneous tissue when the subcutaneous tissue is drawn away. The handle may also have an elongated rod extending from the opposite end of the handle that allows the retractor to be maneuvered into the desired position by the surgeon and then fixed in the desired relative position by clamping or grasping the retractor with the available operating table mechanisms.

The first blade section has a first blade proximal end, a first blade distal end, a first blade outer surface, and a first blade inner surface. Similarly, the second blade section, which is preferably substantially transparent, has a second blade proximal end, a second blade distal end, a second blade outer surface and a second blade inner surface. The second blade outer surface of the second blade section is connected to the first blade section inner surface of the first blade section such that the first and second blade sections are substantially parallel.

The first blade proximal end has a rounded shape or a smoothly radiused pointed shape that allows the retractor to be pushed into the small incision made by the surgeon and thrust forward and maneuvered through the connective tissue between the subcutaneous tissue and the vessel to be harvested. Similarly, the proximal end of the second blade section has a rounded shape or, alternatively, a smoothly radiused pointed shape. The shape of the second blade section proximal end is preferably complementary to the shape of the first blade section proximal end so that the proximal end of the retractor, when the first and second blade sections are connected, can readily penetrate the connective tissue under the subcutaneous tissue as the retractor is inserted into the small incision and maneuvered into position.

The illuminated surgical retractor may also have a bent dissecting tip which extends from the first blade section at the proximal end of the first blade section. This bent dissecting tip allows the surgeon to use the bent tip as a dissecting device as the retractor is inserted and maneuvered around and/or through the connective tissue surrounding the vessel to be harvested.

In order to enhance the reflective qualities of the illuminate retractor, the first blade inner surface of the first blade section preferably has a mirrored surface. Also, the second blade inner surface of the second blade section preferably has a graded dot screen surface. The mirrored surface of the first blade inner surface and the graded dot screen surface of the second blade inner surface act to minimize the light intensity loss of the light energy that is provided to the surgical field by the illuminated retractor.

The connector of the retractor is coupled to the illumination input end that is defined by the distal end of the second blade section. The connector is adapted to receive and releasably retain a distal connector of a light cable that is connected to a source of illumination so that the illumination input end is optically coupled to the source of illumination, thereby allowing light energy to enter the second blade section via the illumination input end. The light energy fills the second blade section and turns the second blade section into a "light pipe." The light energy is, in turn, radiated from the second blade section into the subcutaneous space between the vessel and the subcutaneous tissue exposed by the retractor. In this manner, light can be provided from the light source via the cable to the illumination input end of the second blade section so that the second blade section is illuminated, which results in an illuminated surgical field.

BRIEF DESCRIPTION OF THE FIGURES OF THE DRAWINGS

Embodiments of the invention are described by way of example with reference to the accompanying drawings, in which:

FIG. 5A is a perspective view of a first bayonet member and a second bayonet showing the capture of the distal end of the second blade section;

FIG. 5B is a fragmentary cross-sectional view of a bayonet fastener with the distal end of the second blade section secured;

FIG. 6A is an exploded perspective view of a fourth embodiment of an illuminated retractor according to the present invention;

FIG. 6B is an exploded cross-sectional view of the illuminated retractor shown in FIG. 6A;

FIG. 7 is an exploded perspective view of a fifth embodiment of the illuminated retractor of the present invention showing the bent dissecting tip of the retractor;

FIG. 8 is a fragmentary top-view of the bent tip outer surface showing the dissecting serrations of the illuminated retractor shown in FIG. 7;

FIG. 9 is a fragmentary cross-sectional view of the first blade section taken through line 9–9 of the illuminated retractor shown in FIG. 7 showing the profile of the dissecting serrations in the bent tip of the retractor and the obtuse angle formed between the bent tip and the extended longitudinal axis of the first blade section.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending on the context in which it is used.

The present invention provides for an illuminated retractor for illuminating the subcutaneous space between a vessel, such as the saphenous vein which is located in a patient's leg, and the subcutaneous tissue when the illuminated retractor is used to retract the tissue away from the superior surface of the vessel.

Figures 1, 2A, 2B:
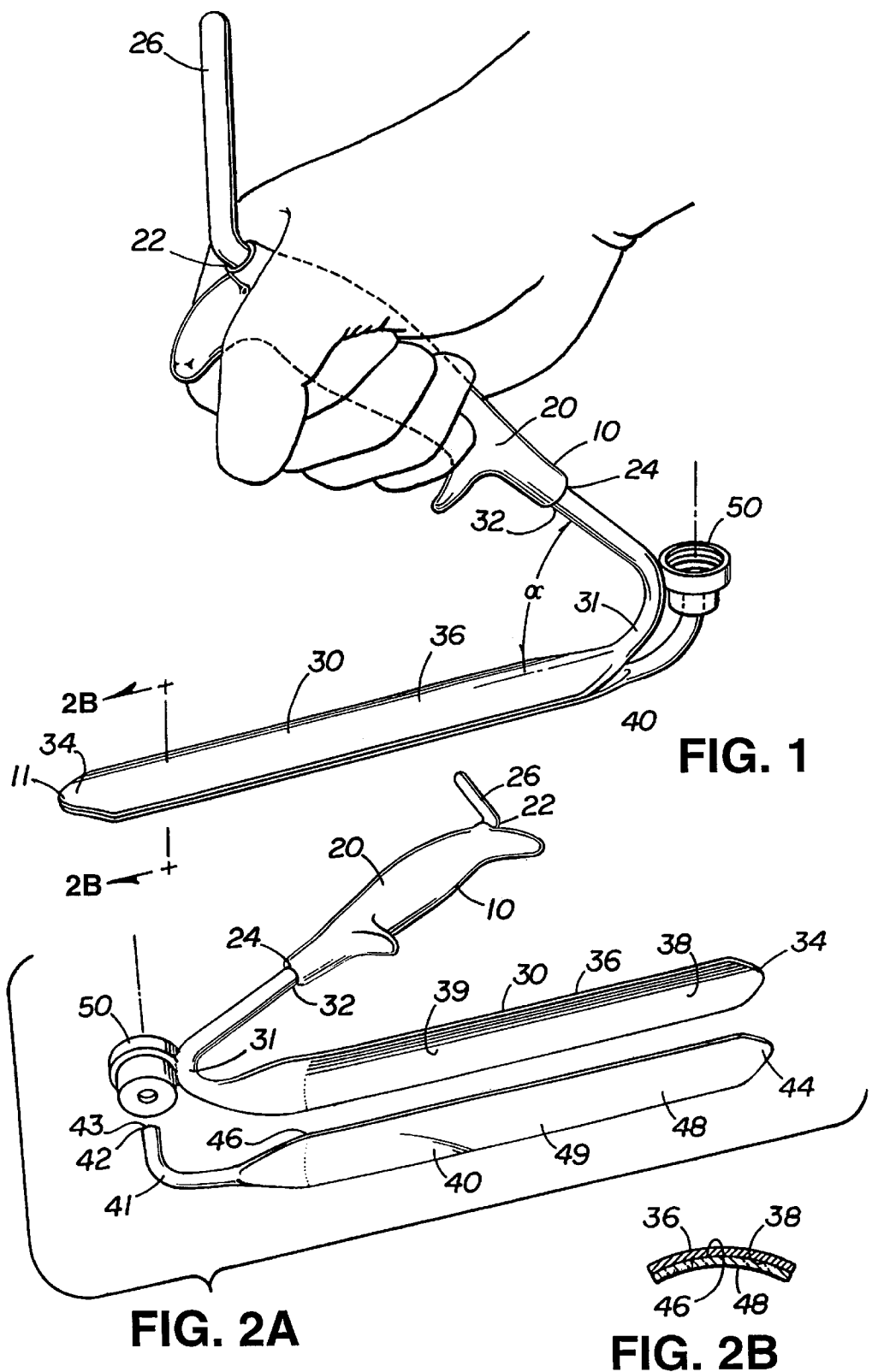
FIG. 1 is a perspective view of the manipulation of an illuminated retractor according to the present invention.
FIG. 2A is an exploded perspective view of the illuminated retractor according to the present invention.
FIG. 2B is a cross-sectional view of the first and second blade sections of the illuminated retractor shown in FIG. 1.

Referring first to FIGS. 1 and 2A, there is shown a first embodiment of the present invention encompassing an illuminated surgical retractor 10 having a handle 20, a first blade section 30, a second blade section 40, and a connector 50.

The handle 20 has a first handle end 22 and a second handle end 24. The second handle end 24 of the handle 20 is connected to the first blade section 30 at the distal end 32 of the first blade section 30 for permitting one-handed use by the surgeon. The angle α formed by the handle 20 and the first blade section 30 is acute and is preferably between 30° and 65°. The best combination of retractor mobility and application of retractive pulling force occurs when the acute angle α between the handle 20 and the first blade section 30 is approximately 45°. The handle 20 permits the retractor 10 to be lifted at any angle with respect to the axis of the vein and, when a pulling force is applied to the handle 20, a retractive force is applied to the subcutaneous tissue via the first blade section 30 which creates subcutaneous space beneath the subcutaneous tissue when the subcutaneous tissue is drawn away. The handle 20 of the retractor 10 is also preferably contoured to be gripped by the hand of a surgeon thus providing more tactile feel and feedback as well as increasing the surgeon's comfort in using and maneuvering the retractor.

The handle 20 may also have an elongated rod 26 extending from the first handle end 22. The elongated rod 26 allows the retractor 10 to be fixed or grasped by operating table mechanisms known in the art so that the retractor 10 may be fixed in position. The elongated rod 26 allows the retractor 10 to be maneuvered into the desired position by the surgeon and then fixed in the desired relative position thus freeing both of the surgeon's hands for the dissection of the exposed vessel.

The first blade section 30 has a first blade proximal end 34, a first blade distal end 32, a first blade outer surface 36, and a first blade inner surface 38. As shown in FIG. 2A, the first blade outer surface 36 and the first blade inner surface 38 extend from the proximal end 34 of the first blade section 30 to near the distal end 32 of the first blade section 30. More specifically, as the first blade section 30 nears the first blade distal end 32, the first blade section 30 tapers into a shaft shape 31 which then bends to form the preferred acute angle α with the handle 20. The first blade outer surface 36 and the first blade inner surface 38 correspondingly are eliminated as the first blade section 30 tapers into the shaft shape 31. As previously noted, the first blade distal end 32 is connected to the second handle end 24 of the handle 20. The first blade proximal end 34 has a rounded shape or a smoothly radiused pointed shape that allows the retractor 10 to be pushed into the small incision made by the surgeon and thrust forward and maneuvered through the connective tissue between the subcutaneous tissue and the vessel to be harvested.

The second blade section 40 has a second blade proximal end 44, a second blade distal end 42, a second blade outer surface 46 and a second blade inner surface 48. As shown in FIG. 2A, the second blade outer surface 46 and the second blade inner surface 48 extend from the proximal end 44 of the second blade section 40 to near the distal end 42 of the second blade section 40. More specifically, as the second blade section 40 nears the second blade distal end 42, the second blade section 40 tapers into a shaft shape 41 which then bends. This bend in the second blade section 40 allows the distal end 42 of the second blade section 40 to remain substantially relatively parallel to the first blade section 30 as the first blade section 30 bends. The second blade outer surface 46 and the second blade inner surface 48 correspondingly are eliminated as the second blade section 40 tapers into the shaft shape 41.

The second blade section 40 is preferably substantially transparent and is preferably made of a transparent plastic, such as a transparent acryl resin, which has the benefit of being highly resistant to breakage while retaining the ability to flex or deform under pressure and then return undamaged to the original, unstressed configuration. However, the second blade section 40 can also be made of glass or other types of known substantially transparent material.

The second blade outer surface 46 of the second blade section 40 is connected to the first blade inner surface 38 of the first blade section 30 such that the first and second blade sections 30, 40 are substantially parallel along the substantial length of the first and second blade sections 30, 40. The second blade section 40 may be connected to the first blade section 30 in any manner known in the art that is within the level of ordinary skill of one in the surgical field.

As shown in FIG. 2A, the second blade outer surface 46 may be chemically bonded to the first blade inner surface 38 through the use of an adhesive or by other chemical bonding means known to one skilled in the art. This chemical bonding may permanently affix the first and second blade sections 30, 40 or may preferably allow the first and second blade sections 30, 40 to be releasably connected for ease of sterilization of the respective blade sections 30, 40. Alternatively, the second blade section 40 may be mechanically fixed to the first blade section 30, by means apparent to one skilled in the art, such that the first and second blade sections 30, 40 may be releasably connected to each other.

The second blade proximal end 44 of the second blade section 40 has a rounded shape or, alternatively, a smoothly radiused pointed shape. The shape of the second blade proximal end 44 is preferably complementary to the shape of the first blade proximal end 34 so that the proximal end 11 of the retractor 10, when the first and second blade sections 30, 40 are connected, can readily penetrate the connective tissue under the subcutaneous tissue as the retractor is inserted into the small incision and maneuvered into position.

As illustrated in FIG. 2B, the first blade section 30 preferably has a curved cross-sectional shape. The curved cross-section of the first blade section 30 causes the first blade outer surface 36 to be convex. The convex cross-sectional shape of the first blade outer surface 36 of the first blade section 30 aids in the prevention of unnecessary trauma to the retracted tissue, as the first blade outer surface 36, which is in contact with the subcutaneous tissue when the pulling force is applied to the retractor 10, presents no sharp edges that could cause tearing of the tissue. Rather, the shape aids in distributing the force applied to the retracted tissue by the first blade section 30.

Still referring to FIG. 2B, the first blade inner surface 38 of the first blade section 30 is preferably concave in cross-section. The outer surface 46 of the second blade section 40 may define a convex curve in cross-section that is complementary to the preferred concave cross-sectional shape of the inner surface 38 of the first blade section 30. As will be obvious to one skilled in the art, if a complementary fit of the outer surface 46 of the second blade section 40 and the inner surface 38 of the first blade section 30 is desired, the outer surface 46 of the second blade section 40 may have any geometric cross-section that allows the second blade outer surface 46 to complementarily fit against the inner surface 38 of the first blade section 30, as there is no requirement that the first blade inner surface 38 be concave in cross-section.

There is no constraint requiring that the outer surface 46 of the second blade section 40 be complementarily shaped to the inner surface 38 of the first blade section 30 The only constraint on the shape of the geometric cross-section of the second blade section 40 is that the chosen geometric cross-section should allow the second blade section 40 to be connected, by means know in the art, to the first blade section 30 such that the first and second blade sections 30, 40 are connected and substantially parallel.

The inner surface 48 of the second blade section 40 may be concave in cross-section. Alternatively, the inner surface 48 of the second blade section 40 could be substantially flat or convex in cross-section.

In order to enhance the reflective qualities of the illuminate retractor 10, the first blade inner surface 38 of the first blade section 30 preferably has a mirrored surface 39. Also, the second blade inner surface 48 of the second blade section 40 preferably has a graded dot screen surface 49. The mirrored surface 39 of the first blade inner surface 38 and the graded dot screen surface 49 of the second blade inner surface 48 act to minimize the light intensity loss of the light that is provided to the surgical field by the illuminated retractor 10.

The illumination input end 43 at the second blade distal end 42 of the second blade section 40 allows light energy to enter the second blade section 40. The light energy fills the second blade section 40, turning the second blade section 40 into a "light pipe." The light energy is, in turn, radiated from the second blade section 40, and particularly from the inner surface 48 of the second blade section 40, into the subcutaneous space between the vessel and the subcutaneous tissue exposed by the retractor 10. Since substantially the entire length of the second blade section 40 is illuminated, a large, well illuminated surgical field, extending the substantial length of the second blade section 40 of the retractor 10, is provided for the surgeon to operate. This allows the surgeon to dissect the vein in an minimally invasive manner without the need for viewing the surgical field through endoscopic visual devices.

The connector 50 is coupled to the illumination input end 43 which is defined by the distal end 42 of the second blade section 40 of the retractor 10. The connector 50 is adapted to receive and releasably retain a distal connector (not shown) of a light cable [not shown] that is connected to a source of illumination (not shown) so that the illumination input end 43 is optically coupled to the source of illumination. In this manner, light can be provided from the light source via the cable to the illumination input end 43 of the second blade section 40 so that the second blade section 40 is illuminated.

Figure 3:
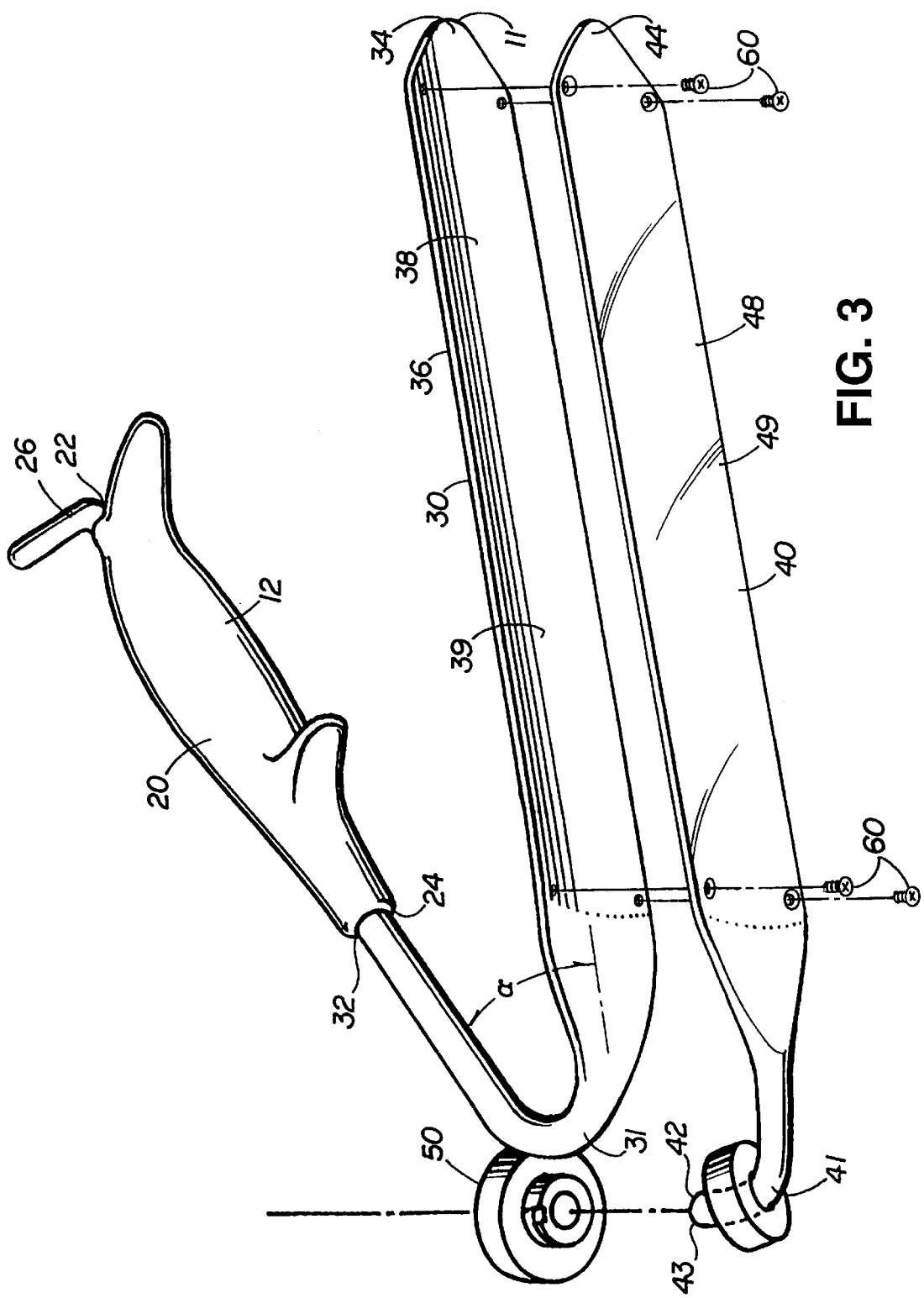
FIG. 3 is an exploded perspective view of a second embodiment of an illuminated retractor according to the present invention.

FIG. 3 shows a second embodiment of a illuminated retractor 12 of the present invention. The construction of the second embodiment is similar to the first embodiment and, accordingly, uses the same reference numbers for similar components. The components in FIG. 3 that use the same reference numerals as in FIGS. 1–2B are substantially equivalent and, therefore, the description thereof is omitted for the second embodiment. The second embodiment of the present invention encompasses an illuminated surgical retractor 12 having a handle 20, a first blade section 30, a second blade section 40, a means for connecting the first and second blade sections, and a connector 50.

Still referring to FIG. 3, the means for connecting the first blade section 30 to the second blade section 40 preferably comprises a plurality of screws 60, or, alternatively, bolts, releasably connecting the outer surface 46 of the second blade section 40 to the inner surface 38 of the first blade section 30. It is preferable to locate the screws 60 along the periphery of the second blade section 40 to minimize the shadows caused by the screws 60, which could degrade the light illumination of the retractor 12.

Figures 4, 4A, 4B:
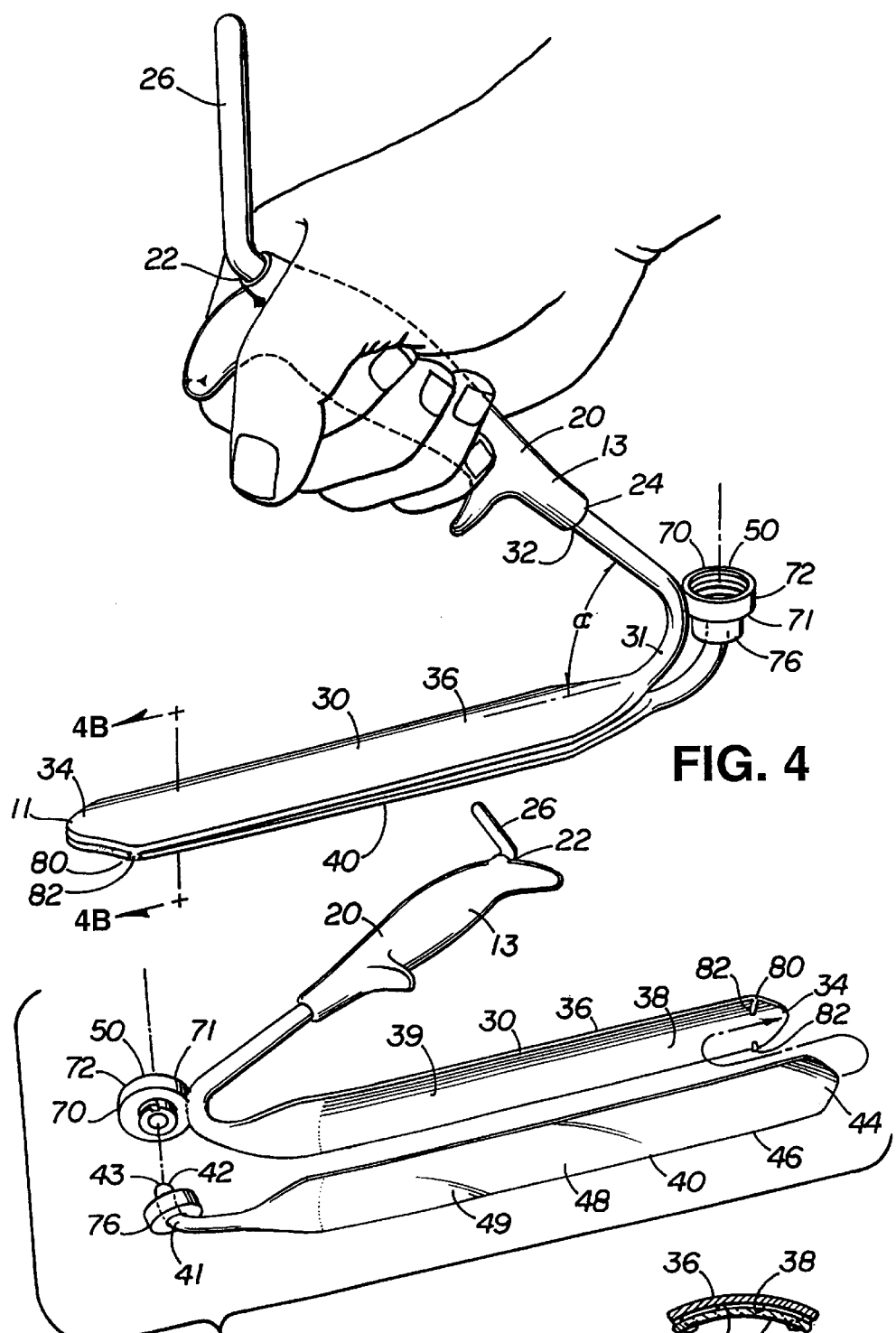
FIG. 4 is a perspective view of the manipulation of a third embodiment of an illuminated retractor according to the present invention.
FIG. 4A is an exploded perspective view of a third embodiment of the illuminated retractor according to the present invention.
FIG. 4B is a cross-sectional view of the first and second blade sections of the illuminated retractor shown in FIG. 4.

FIGS. 4–4B show a third embodiment of an illuminated retractor 13 of the present invention. The construction of the third embodiment is similar to the first embodiment and, accordingly, the figures use the same reference numbers for similar components. The components in FIGS. 4–4B that use the same reference numerals as in FIGS. 1–2B are substantially equivalent and, therefore, the description thereof is omitted for the third embodiment. The third embodiment of the present invention encompasses an illuminated surgical retractor 13 having a handle 20, a first blade section 30, a second blade section 40, a means for connecting the first and second blade sections, and a connector 50.

Referring to FIG. 4A, the means for connecting the first blade section 30 to the second blade section 40 comprises a socket means 70 and a pinning means 80. The socket means 70 releasably receives the distal end 42 of the second blade section 40 while the pinning means 80 releasably receives the proximal end 44 of the second blade section 40 so that the second blade section 40 may be releasably connected to the first blade section 30. Referring to FIGS. 4A–4B and 5A–5B, the socket means 70 is preferably a bayonet fastener 71 having a first bayonet member 72 that is connected to the first blade section 30 near the distal end 32 of the first blade section 30 and a second bayonet member 76 that is connected to the second blade section 40 near the distal end 42 of the second blade section 40. The first bayonet member 72 and the second bayonet member 76 are complementarily sized and shaped so that the first bayonet member 72 and the second bayonet member 76 may be complementarily releasably engaged. Preferably, the first bayonet member 72 has an exterior first bayonet surface having a threaded surface 90 and the second bayonet member 76 has a complementary threaded interior second bayonet surface 92.

Preferably, the first bayonet member 72 has a first top surface 73 and a first bottom surface 74. A first bore 75 extends through the first bayonet member 72 from the first top surface 73 to the first bottom surface 74. Similarly, the second bayonet member 76 has a second top surface 77 and a second bottom surface 78 having a second bore 79 extending therethrough from the first top surface 73 to the first bottom surface 74. The second top surface 77 of the cap member defines a indented cap shape 91 having the threaded interior second bayonet surface 92 and a shoulder surface 94. The shoulder surface 94 surrounds the second bore 79 of the second bayonet member 76. Preferably, the second bore 79 is a keyway 96. The first bore 75 of the first bayonet member 72 and the second bore 79, i.e., the keyway 96, of the second bayonet member 76 are substantially co-axially aligned when the first bayonet member 72 and the second bayonet member 76 are engaged.

The distal end 42 of the second blade section 40, which preferably has a shaped lip 45 around the distal end 42 of the second blade section 40 that matches the defined shape of the keyway 96 of the second bayonet member 76, can thereby extend into and through the keyway 96 of the second bayonet member 76. The distal end 42 of the second blade section 40 is then secured relative to the first blade section 30 upon the rotation of the second bayonet member 76 relative to the fixed first bayonet member 72. This rotation causes the keyway 96 of the second bayonet member 76 to correspondingly rotate, thus securing the shaped lip 45 of the distal end 42 of the second blade section 40 and preventing the detachment of the distal end 42 of the second blade section 40.

When secured, the distal end 42 of the second blade section 40 projects above the shoulder surface 94 of the second bayonet member 76. This allows the illumination input end 43, located at the distal end 42 of the second blade section 40, to be disposed near the first bore 75 of the first bayonet member 72 when the first and second bayonet members 72, 76 are engaged. The first top surface 73 of the first bayonet member 72 is shaped and adapted to act as the connector 50 for the retractor 13, thereby allowing the connector 50 at the first top surface 73 of the first bayonet member 72 to receive and releasably retain a distal connector (not shown) of a light cable (not shown) that is connected to a source of illumination (not shown) so that the illumination input end 43 of the second blade section 40 is optically coupled to the source of illumination. In this manner, light can be provided from the light source via the cable to the illumination input end 43 of the second blade section 40, so that the second blade section 40 is illuminated.

Referring to FIG. 4A, the pinning means 80 is preferably a plurality of angled pins 82 extending from the inner surface 38 of the first blade section 30 near the proximal end 34 of the first blade section 30. The pins are sized so that the first and second blade sections 30, 40 are mated to each other, forcing the second blade section 40 into close cooperation with the first blade section 30, when the proximal end 44 of the second blade section 40 is inserted underneath the pins 82. The pins 82 grasp and secure the abutting portions of the second blade section 40 near the proximal end 44 of the second blade section 40 when the first and second bayonet members 72, 76 are complementarily engaged.

When the first blade section 30 and the second blade section 40 are connected by the bayonet fastener 71 and the plurality of pins 82 in the fashion described above, the cross-sectional shape of the outer surface 46 of the second blade section 40 may be, but is not required to be, complementarily shaped to the cross-sectional shape of the inner surface 38 of the first blade section 30.

FIGS. 6A–6B show a fourth embodiment of a illuminated retractor 14 of the present invention. This embodiment is a variation of the third embodiment. Specifically, the pinning means 80 is varied. The construction of the fourth embodiment is similar to the first and third embodiments and, accordingly, the figures use the same reference numbers for similar components. The components in FIGS. 6A–6B that use the same reference numerals as in FIGS. 1–5B are substantially equivalent and, therefore, the description thereof is omitted for the fourth embodiment.

The fourth embodiment of the present invention encompasses an illuminated surgical retractor 14 having a handle 20, a first blade section 30, a second blade section 40, a means for connecting the first and second blade sections, and a connector 50. Referring to FIG. 6A, the means for connecting the first blade section 30 to the second blade section 40 comprises a socket means 70 and a pinning means 80. The socket means 70 releasably receives the distal end 42 of the second blade section 40 while the pinning means 80 releasably receives the proximal end 44 of the second blade section 40, so that the second blade section 40 may be releasably connected to the first blade section 30. The socket means 70 used in the fourth embodiment is preferably the same as described for the third embodiment above. The pinning means 80 used in the fourth embodiment is preferably a plurality of tabs 84 extending from the inner surface 38 of the first blade section 30 near the proximal end 34 of the first blade section 30. The tabs 84 are sized so that the second blade section 40 is forced into cooperation with the first blade section 30 when the proximal end 44 of the second blade section 40 is inserted into close cooperation with the tabs 84. The preferred shape of the tabs 84 is a dovetail shape, however other geometric shapes are contemplated.

The tabs 84 grasp and secure the abutting portions of the second blade section 40 near the proximal end 44 of the second blade section 40 when the first and second bayonet members 72, 76 are complementarily engaged. Referring to FIG. 6B, the tabs 84 define a grasping surface 86 between the upper surface 85 of the tabs 84 and the first blade inner surface 38. The grasping surface 86 of the tabs 84 preferably forms an acute angle Δ with the inner surface 38 of the first blade section 30. This acute angle Δ of the grasping surface 86 aids in mechanically forcing and retaining the second blade section 40 in cooperation with the first blade section 30. The tabs 84 have the added advantage of not extending above the second blade inner surface 48 of the second blade section 40 when the first blade section 30 is connected to the second blade section 40, as the upper surface 85 of the tabs 84 is substantially planer to the outer surface 46 of the second blade section 40, so that the proximal end 11 of the retractor 14 is substantially smooth and presents no projections that could inflict unnecessary trauma on the patient's tissues or to the operating physician's hands.

The combination of the bayonet fastener 71 and the tabs 84 act to secure the second blade section 40 to the first blade section 30 so that the illuminated retractor 14 can be used in a surgical environment in which force is required to be applied to the retractor 14, via the handle 20, in order to expose the necessary subcutaneous space between the vessel to be harvested and the subcutaneous tissue. However, the bayonet fastener 71 and the tabs 84 also allow the second blade section 40 to be separated from the first blade section 30 by simply rotating the second bayonet member 76 to align the keyway 96 of the second bayonet member 76 with the shaped lip 43 of the distal end 42 of the second blade section 40, which has a complementary key shape, withdrawing the distal end 42 of the second blade section 40 from the keyway 96 of the second bayonet member 76, and pulling the second blade section 40 free of the tabs 84 extending from the inner surface 38 of the first blade section 30. This allows the first and second blade sections 30, 40 to be readily separated for ease of sterilization of the retractor 14 components or for the replacement of the second blade section 40.

When the first blade section 30 and the second blade section 40 are connected by the bayonet fastener 71 and the plurality of tabs 84 in the fashion described above, the cross-sectional shape of the outer surface 46 of the second blade section 40 may be, but is not required to be complementarily shaped to the cross-sectional shape of the inner surface 38 of the first blade section 30.

FIGS. 7–9 show a fifth embodiment of an illuminated retractor 15 of the present invention. The construction of the fifth embodiment is similar to the first and fourth embodiments and, accordingly, the figures use the same reference numbers for similar components. The components in FIGS. 7–9 that use the same reference numerals as in FIGS. 1–6B are substantially equivalent and, therefore, the description thereof is omitted for the fifth embodiment.

The fifth embodiment of the present invention encompasses an illuminated surgical retractor 15 having a handle 20, a first blade section 30, a second blade section 40, a bent tip 100, and a connector 50. The first blade section 30 may be connected to the second blade section 40 in any manner known in the art that is within the level of ordinary skill of one in the surgical field. The second blade outer surface 46 of the second blade section 40 may be chemically bonded to the first blade inner surface 38 of the first blade section 30 through the use of an adhesive or by other chemical bonding means known to one skilled in the art. This chemical bonding may permanently affix the first and second blade sections 30, 40 or it may preferably allow the first and second blade sections 30, 40 to be releasably connected for ease of sterilization of the respective blade sections 30, 40. Alternatively, the second blade section 40 may be mechanically fixed to the first blade section 30, by means apparent to one skilled in the art, such that the first and second blade sections 30, 40 may be releasably connected to each other.

Preferably, as shown in FIG. 7, the first blade section 30 is connected to the second blade section 40 by a socket means 70 and a pinning means 80. The socket means 70 releasably receives the distal end 42 of the second blade section 40 while the pinning means 80 releasably receives the proximal end 44 of the second blade section 40, so that the second blade section 40 may be releasably connected to the first blade section 30. The socket means 70 used in the fifth embodiment is preferably the same as described for the third embodiment above. The pinning means 80 used in the fifth embodiment is preferably the same as described for the fourth embodiment above.

The first blade section 30 has a first blade section proximal end 34, a first blade section distal end 32, a first blade outer surface 36, and a first blade inner surface 38. As shown in FIG. 7, the first blade outer surface 36 and the first blade inner surface 38 extend from the proximal end 34 of the first blade section 30 to near the distal end 32 of the first blade section 30. More particularly, as the first blade section 30 nears the first blade distal end 32, the first blade section 30 tapers into a shaft shape 31 which then bends to form the preferred acute angle α with the handle 20. In the fifth embodiment, the preferred acute angle α is approximately 60 degrees. The first blade outer and inner surfaces 36, 38 correspondingly taper as the first blade section 30 tapers into the shaft shape 31. As previously noted, the first blade distal end 32 is connected to the second handle end 24 of the handle 20.

Still referring to FIG. 7, the second blade section 40 has a second blade proximal end 44, a second blade distal end 42, a second blade outer surface 46, and a second blade inner surface 48. The second blade outer and inner surfaces 46, 48 extend from the proximal end 44 of the second blade section 40 to near the distal end 42 of the second blade section 40. More specifically, as the second blade section 40 nears the second blade distal end 42, the second blade section 40 tapers into a shaft shape 41 which then bends. This bend in the second blade section 40 allows the distal end 42 of the second blade section 40 to remain substantially relatively parallel to the first blade section 30 as the first blade section 30 bends.

To aid in the dissection of the connective tissue and to more efficiently use the force applied to the retractor 15 as the retractor 15 is maneuvered through and around the connective tissue, this embodiment uses a bent tip 100 having a bent tip distal end 101 which is connected to the proximal end 34 of the first blade section 30. Preferably, the bent tip 100 extends, as a simple extension, from the proximal end 34 of the first blade section 30. As shown in FIG. 9, the bent tip 100, having a bent tip longitudinal axis T, forms an obtuse angle θ relative to a first blade section longitudinal axis L. This obtuse angle θ can be between 95°–175° and is preferably approximately 160°.

Referring to FIG. 8, the bent tip proximal end 102 has a rounded shape or a smoothly-radiused pointed shape that allows the retractor 15 to be pushed into the small incision made by the surgeon and maneuvered through the connective tissue between the subcutaneous tissue and the vessel to be harvested. The bent tip 100 further has a bent tip outer surface 104 having a plurality of dissecting serrations 106. Each of these serrations 106 are preferably at a substantial right angle to the bent tip longitudinal axis T and preferably extend substantially across the width of the bent tip 100. It is contemplated that the serrations 106 may be placed at an angle, other than the right angle described above, relative to the bent tip longitudinal axis T. It is also contemplated that the serrations 106 might be placed at series of angles to form a graphic series of serrations 106. One example of which would be the use of a plurality of arrow, or v-shaped, serrations 106 with the point of the arrow oriented toward the proximal end 102 of the bent tip 100.

As shown in FIG. 9, the dissecting serrations 106 preferably have a saw-tooth cross-sectional profile 108. This profile 108 allows the serrations 106 to aid in dissecting intervening connective tissue when the retractor 15 is pressed forward into the subcutaneous space and lifted or withdrawn slightly from the subcutaneous space. It is contemplated that other geometric cross-sectional profiles of the serrations 106, such as a triangle profile, may also be used.

Preferably, as shown in FIGS. 7 and 9, both the first blade outer and inner surfaces 36, 38 preferably have a curved cross-sectional shape. This curved cross-sectional shape causes the first blade outer surface 36 to be convex and the first blade inner surface to be concave 38. The outer surface 46 of the second blade section 40 may have a convex cross-sectional shape that is complementary to the concave cross-sectional shape of the inner surface 38 of the first blade section 30. However, there is no requirement or constraint that the second blade outer surface 46 must have a complementary cross-sectional shape to the inner surface 38 of the first blade section 30.

Still referring to FIGS. 7 and 9, the bent tip 100 preferably has a substantially planer or flat cross-sectional shape. Alternatively, the bent tip 100 could have a curved cross-sectional shape which is complementary to the curved cross sectional shape of the first blade outer surface 36.

The purpose of the bent tip 100 of the retractor 15 of this embodiment is to help the surgeon translate some of the applied force to the retractor 15 into a dissecting force by letting the bent tip 100, with the dissecting serrations 106, perform some of the required dissecting work. By having the retractor 15 accomplish some of the dissecting required by the vessel harvesting procedure, the surgeon can, while still performing in a minimally invasive manner, more rapidly complete the surgical procedure, which results in reduced surgical time and possibility of trauma to the patient from the surgery.

The present invention has been described in reference to use in harvesting blood vessels. It would be obvious to one skilled in the art that the present invention could also be used in other minimally invasive surgical procedures in which the illumination of the minimally invasive surgical field is desired.

Although only four types of connecting means are shown in FIGS. 2A–6B for detachably connecting the second blade section 40 to the first blade section 30 of the retractor, any type of connecting means can be utilized. Thus, the detachable connection feature of the second blade section 40 of the present invention is not limited to the connecting means described above, but, rather, can be connected in a manner well within the level of ordinary skill of one in the surgical field. Furthermore, although the present invention has been described with reference to specific details of certain embodiments thereof, it is not intended that such detail should be regarded as limitations upon the scope of the invention except as and to the extent that they are included in the accompanying claims.

What is claimed is:

1. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, said second blade section connected to said first blade section such that said first and second blade sections are substantially parallel, the second blade distal end of said second blade section defining an illumination input end; and a connector coupled to the illumination input end, said connector adapted to optically couple the illumination input end to a source of illumination so that said second blade section is substantially illuminated.

2. The illuminated surgical retractor of claim 1, wherein said first blade section has a first blade outer surface that defines a convex curve in cross-section, and wherein the first blade inner surface of said first blade section defines a concave curve in cross-section.

3. The illuminated surgical retractor of claim 2, wherein the second blade outer surface of said second blade section defines a convex curve in cross-section complementary to the second blade inner surface and wherein the second blade inner surface of said second blade section defines a concave curve in cross-section.

4. The illuminated surgical retractor of claim 1, wherein said second blade section is substantially transparent.

5. The illuminated surgical retractor of claim 1, wherein the acute angle formed between said handle and said first blade section is from 30° to 65°.

6. The illuminated surgical retractor of claim 1, wherein said handle is contoured to be gripped by a hand of an operator.

7. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section, wherein the first blade inner surface has a mirrored finish;

a second blade section having a second blade proximal end, a second blade distal end, a second blade outer surface, extending from the second blade proximal end to near the second blade distal end, and a second blade inner surface, extending from the second blade proximal end to near the second blade distal end, said second blade section connected to said first blade section such that said first and second blade sections are substantially parallel, the second blade distal end of said second blade section defining an illumination input end; and a connector coupled to the illumination input end, said connector adapted to optically couple the illumination input end to a source of illumination so that said second blade section is substantially illuminated.

8. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, said second blade section connected to said first blade section such that said first and second blade sections are substantially parallel, the second blade distal end of said second blade section defining an illumination input end; and a connector coupled to the illumination input end, said connector adapted to optically couple the illumination input end to a source of illumination so that said second blade section is substantially illuminated, wherein said handle has an elongated rod extending from the first handle end.

9. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

means for connecting said second blade section to said first blade section such that said first and second blade sections are substantially parallel; and a connector coupled to the illumination input end, said connector being adapted to optically couple the illumination input end to a source of illumination so that said second blade section is substantially illuminated.

10. The illuminated surgical retractor of claim 9, wherein said connecting means comprises a plurality of screws releasably connecting said second blade section to said first blade section.

11. The illuminated surgical retractor of claim 9, wherein said connecting means comprises an adhesive applied to the first blade inner surface to which the second blade outer surface is affixed whereby said second blade section adheres to said first blade section.

12. The illuminated surgical retractor of claim 9, wherein said first blade section has a first blade outer surface that defines a convex curve in cross-section, and wherein the first blade inner surface of said first blade section defines a concave curve in cross-section.

13. The illuminated surgical retractor of claim 12, wherein the second blade outer surface of said second blade defines a convex curve in cross-section complementary to the first blade inner surface, and wherein the second blade inner surface of said second blade section defines a concave curve in cross-section.

14. The illuminated surgical retractor of claim 9, wherein said second blade section is substantially transparent.

15. The illuminated surgical retractor of claim 9, wherein the acute angle formed between said handle and said first blade section is from 30° to 65°.

16. The illuminated surgical retractor of claim 9, wherein said handle is contoured to be gripped by a hand of an operator.

17. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section, wherein the first blade inner surface has a mirrored finish;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

means for connecting said second blade section to said first blade section such that said first and second blade sections are substantially parallel; and a connector coupled to the illumination input end, said connector being adapted to optically couple the illumination input end to a source of illumination so that said second blade section is substantially illuminated.

18. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

means for connecting said second blade section to said first blade section such that said first and second blade sections are substantially parallel; and a connector coupled to the illumination input end, said connector being adapted to optically couple the illumination input end to a source of illumination so that said second blade section is substantially illuminated, wherein said handle has an elongated rod extending from the first handle end.

19. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

a bayonet fastener;

a plurality of tabs, said second blade section connected to said first blade section by said bayonet fastener and said plurality of tabs such that said first blade section and said second blade section are substantially parallel;

said bayonet fastener comprising a first bayonet member connected near the first blade distal end of said first blade section, and a second bayonet member, releasably connected near the second blade distal end of said second blade section, so that said first bayonet member and said second bayonet member may be complementarily engaged;

said plurality of tabs extending from the first inner surface of said first blade section proximate the first blade proximal end, such that said tabs may grasp said second blade section proximate the second blade proximal end when said first and second bayonet members are complementarily engaged; and a connector coupled to the illumination input end, said connector adapted to optically couple the illumination input end to a source of illumination so that said second blade section is substantially illuminated.

20. The illuminated surgical retractor of claim 19, wherein said tabs do not extend above the second blade inner surface when said first blade section is connected to said second blade section.

21. The illuminated surgical retractor of claim 19, wherein said first bayonet member has a first top surface and a first bottom surface defining a first bore extending therebetween, wherein said second bayonet member has a second top surface and a second bottom surface defining a second bore extending therebetween, and wherein the second blade distal end extends therethrough the second bore of said second bayonet member so that the illumination input end is disposed near the first bore of said first bayonet member when said first and second blade sections are connected.

22. The illuminated surgical retractor of claim 21, wherein the first top surface of said first bayonet member is adapted to act as said connector, said connector adapted to optically couple the illumination input end to the source of illumination.

23. The illuminated surgical retractor of claim 19, wherein said first blade section has a first blade outer surface that defines a convex curve in cross-section, and wherein the first blade inner surface of said first blade section defines a concave curve in cross-section.

24. The illuminated surgical retractor of claim 23, wherein the second blade outer surface of said second blade section defines a convex curve in cross-section complementary to the first blade inner surface, and wherein the second blade inner surface of said second blade section defines a concave curve in cross-section.

25. The illuminated surgical retractor of claim 19, wherein said second blade section is substantially transparent.

26. The illuminated surgical retractor of claim 19, wherein the acute angle formed between said handle and said first blade section is from 30° to 65°.

27. The illuminated surgical retractor of claim 19, wherein said handle is contoured to be gripped by a hand of an operator.

28. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section, wherein the first blade inner surface has a mirrored finish;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

a bayonet fastener;

a plurality of tabs, said second blade section connected to said first blade section by said bayonet fastener and said plurality of tabs such that said first blade section and said second blade section are substantially parallel;

said bayonet fastener comprising a first bayonet member connected near the first blade distal end of said first blade section, and a second bayonet member, releasably connected near the second blade distal end of said second blade section, so that said first bayonet member and said second bayonet member may be complementarily engaged;

said plurality of tabs extending from the first inner surface of said first blade section proximate the first blade proximal end, such that said tabs may grasp said second blade section proximate the second blade proximal end when said first and second bayonet members are complementarily engaged; and a connector coupled to the illumination input end, said connector adapted to optically couple the illumination input end to a source of illumination so that said second blade section is substantially illuminated.

29. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, the second blade distal end of said second blade section defining an illumination input end;

a bayonet fastener;

a plurality of tabs, said second blade section connected to said first blade section by said bayonet fastener and said plurality of tabs such that said first blade section and said second blade section are substantially parallel;

said bayonet fastener comprising a first bayonet member connected near the first blade distal end of said first blade section, and a second bayonet member, releasably connected near the second blade distal end of said second blade section, so that said first bayonet member and said second bayonet member may be complementarily engaged;

said plurality of tabs extending from the first inner surface of said first blade section proximate the first blade proximal end, such that said tabs may grasp said second blade section proximate the second blade proximal end when said first and second bayonet members are complementarily engaged; and a connector coupled to the illumination input end, said connector adapted to optically couple the illumination input end to a source of illumination so that said second blade section is substantially illuminated, wherein said handle has an elongated rod extending from the first handle end.

30. An illuminated surgical retractor comprising:

a handle having a first handle end and a second handle end;

a first blade section having a first blade proximal end, a first blade distal end, and a first blade inner surface, extending from the first blade proximal end to near the first blade distal end, the second handle end of said handle connected to the first blade distal end of said first blade section such that said handle forms an acute angle with said first blade section;

a second blade section having a second blade proximal end, a second blade distal end, a second blade outer surface, extending from the second blade proximal end to near the second blade distal end, and a second blade inner surface, extending from the second blade proximal end to near the second blade distal end, said second blade section connected to said first blade section such that said first and second blade sections are substantially parallel, the second blade distal end of said second blade section defining an illumination input end;

a bent tip having a bent tip proximal end and a bent tip distal end, the bent tip distal end of said bent tip connected to the first blade proximal end of said first blade section such that said bent tip forms an obtuse angle with said first blade section; and a connector coupled to the illumination input end of the distal end of said second blade section, said connector adapted to optically couple the illumination input end to a source of illumination so that said second blade section is substantially illuminated.

31. The illuminated surgical retractor of claim 30, wherein said bent tip has a tip longitudinal axis and a bent tip outer surface, the bent tip outer surface having a plurality of dissecting serrations at substantially right angles to the tip longitudinal axis and extending substantially across the width of the bent tip.

32. The illuminated surgical retractor of claim 31, wherein said dissecting serrations have a saw-tooth cross-sectional profile.

33. The illuminated surgical retractor of claim 30, wherein the bent tip proximal end of said bent tip has a round shape.

34. The illuminated surgical retractor of claim 30, wherein the bent tip proximal end of said bent tip has a smoothly-radiused pointed shape.

35. The illuminated surgical retractor of claim 30, wherein said bent tip has a substantially flat cross-sectional shape.

36. The illuminated surgical retractor of claim 30, wherein said first blade section has a first blade outer surface that defines a convex curve in cross-section, and wherein the first blade inner surface of said first blade section defines a concave curve in cross-section.

37. The illuminated surgical retractor of claim 36, wherein the second blade outer surface of said second blade section defines a convex curve in cross-section complementary to the first blade inner surface, and wherein the second blade inner surface of said second blade section defines a concave curve in cross-section.

38. The illuminated surgical retractor of claim 30, wherein the first blade inner surface has a mirrored finish.

39. The illuminated surgical retractor of claim 30, wherein said second blade section is substantially transparent.

40. The illuminated surgical retractor of claim 30, wherein the acute angle formed between said handle and said first blade section is from 30° to 65°.

41. The illuminated surgical retractor of claim 30, wherein the obtuse angle formed between said first blade section and said bent tip is from 145° to 175°.

42. The illuminated surgical retractor of claim 30, wherein said handle has an elongated rod extending from the first handle end.

43. The illuminated surgical retractor of claim 30, wherein said handle is contoured to be gripped by a hand of an operator.

* * * * *